United States Patent [19]

Childs

[11] 4,164,616

[45] Aug. 14, 1979

[54] PRODUCTION OF DIHYDROXY ALKANE

[75] Inventor: William V. Childs, Bartlesville, Okla.

[73] Assignee: Phillips Petroleum Company, Bartlesville, Okla.

[21] Appl. No.: 870,157

[22] Filed: Jan. 17, 1978

[51] Int. Cl.$^2$ ................................................ C07C 31/20
[52] U.S. Cl. .................................... 568/858; 560/237; 568/857; 568/861; 260/654 H
[58] Field of Search ................ 560/237; 568/857, 858, 568/861

[56] References Cited

U.S. PATENT DOCUMENTS

| | | | |
|---|---|---|---|
| 2,912,471 | 11/1959 | Capp et al. | 260/654 H |
| 3,584,064 | 6/1971 | Weitz et al. | 260/654 H |
| 3,720,704 | 3/1973 | Sakomura et al. | 560/237 |
| 4,000,185 | 12/1976 | Kurkov et al. | 560/237 |
| 4,001,307 | 1/1977 | Cardenas | 560/237 |
| 4,062,900 | 12/1977 | Tanabe et al. | 568/858 |

OTHER PUBLICATIONS

Hov, "Manufacture of Soda," 2nd ed. (1942), pp. 316, 317.

Primary Examiner—Joseph E. Evans

[57] ABSTRACT

Halogen, e.g., bromine, and a conjugated diene, e.g., butadiene, are reacted in vapor phase, the reacted mass condensed and contacted with alkali metal acetate dissolved or dispersed in an acid, e.g., potassium acetate in glacial acetic acid, thus causing a reaction of formed dibromobutene-2 with the acetate to form diacetoxy-2-butene. The latter is hydrogenated to the corresponding diacetoxylated alkane. The diacetoxy alkane is hydrolyzed to the dihydroxy alkane, e.g., 1,4-butanediol. Alternately, the diacetoxy alkene can be hydrolyzed and the hydrogenation then conducted.

5 Claims, No Drawings

PRODUCTION OF DIHYDROXY ALKANE

This invention relates to the production of 1,4-diacetoxy-2-butene which can be converted to 1,4-butanediol. More particularly the invention relates to a combination of steps in a process which involves utilization of by-products such that the final product can be produced using as only main raw materials fed to the process as a conjugated diene, e.g., butadiene.

In one of its concepts the invention provides a multi-step operation in which a conjugated diene, halogen and an alkali metal acetate dissolved or dispersed in an acid are brought together in a manner and under conditions to produce a diacetoxylated alkene, the diacetoxylated alkene is hydrogenated to the diacetoxylated alkane which is then hydrolyzed. In another of its concepts the invention provides a process in which the hydrolysis is effected prior to the hydrogenation. In a still further concept the invention provides a utilization step in which alkali metal halogen salt is utilized to produce an alkali metal hydroxide, employed in the hydrolysis, hydrogen for the hydrogenation and the halogen used in the first step. In a further concept of the invention still there is provided a multistep process comprising four steps in which the only main raw material which is consumed is a conjugated diene.

1,4-Butanediol is known and is used to produce tetrahydrofuran which is a solvent for high polymers, particularly polyvinylchloride (PVC). Tetrahydrofuran, a well-known chemical raw material, is also used for production of certain fibers and polyurethane elastomers. 1,4-Butanediol is also used in the preparation of polybutylene terephthalate, a recently introduced new engineering plastic having a combination of desirable properties. Uses here described have sharply increased the demand for 1,4-butanediol and therefore for an economically more desirable process for its production.

Thus, the present methods of producing this material are the Reppe process using acetylene and formaldehyde, the process using 1,4-dichlorobutene-2 by-product in the production of chloroprene by the butadiene process, and the maleic anhydride process which forms 1,4-butanediol and tetrahydrofuran by hydrogenation of maleic anhydride. The Reppe process, which is most extensively employed in the world, is encountering a difficulty since its main raw material, acetylene, may not be available in large volumes at stabilized costs as the petrochemical industry grows. A main disadvantage to producing acetylene is the high capital investment needed including that for safety facilities required for its processing which must be carried out under high pressures. The dichlorobutene process requires the additional production of chloroprene from butadiene and chlorine by way of the production of butadiene. The maleic anhydride process uses relatively expensive maleic acid and accompanies tetrahydrofuran production which makes it difficult to attain a high yield of 1,4-butanediol.

Other processes which have been described for the production of 1,4-butanediol include: hydrogenation of gamma-butyrolactone; a four step process involving oxyacetoxylation of propylene followed by hydroformylation, hydrogenation, and hydrolysis; hydrogenation of peroxides of butadiene; and a 1,4-diacetoxybutene-2 process. The latter process is similar to that of the current invention. The current invention is different in that an expensive catalyst is not required. In the 1,4-diacetoxybutene-2 process butadiene is reacted vapor or liquid phase with acetic acid and oxygen in the presence of a palladium catalyst to give a mixture of 1,4- and 3,4-diacetoxy-2-butene. The 3,4-derivative is isomerized to the 1,4-derivative which is hydrogenated and hydrolyzed to 1,4-butanediol.

It is an object of this invention to provide a process for the production of 1,4-butanediol. It is another object of this invention to provide a process for the production of 1,4-diacetoxy-2-butene. A further object of the invention is to provide a diacetoxylated alkane. A still further object of the invention is to provide a diacetoxylated alkene. Another object of the invention is to provide a process employing as raw material used in the process a conjugated diene, said diene being the only material needed to be fed to the process once it has been set up using other ingredients. A still further object of the invention is to provide a non-catalytic operation for the production of the 1,4-diacetoxy alkene, thus minimizing costs which of course would include preparation, recovery and regeneration of catalytic ingredients or catalysts.

Other aspects, concepts and objects of this invention are apparent from a study of this disclosure and the appended claims.

According to the invention, there is provided a process or steps in combination to produce, ultimately, 1,4-alkanediol, by way of 1,4-diacetoxy-2-alkene and 1,4-diacetoxy alkane employing a halogen, an alkali metal acetate, and an acid and, when the operation is under way, using only a conjugated diene as feed to the overall process which, in one of its steps, in its preferred form, regenerates reactants from by-products formed, e.g., alkali metal hydroxide employed in the hydrolysis of the 1,4-diacetoxy alkane to produce the 1,4-alkanediol.

In one of its now preferred forms the invention is applied to the preparation of 1,4-butanediol.

The reactions of the invention can be represented by the following equations.

Step 1.

$CH_2=CH-CH=CH_2 + Br_2 \longrightarrow BrCH_2-CH=CH-CH_2Br$ $BrCH_2-CH=CH-CH_2Br + 2NaOOCCH_3 \xrightarrow{CH_3COOH}$

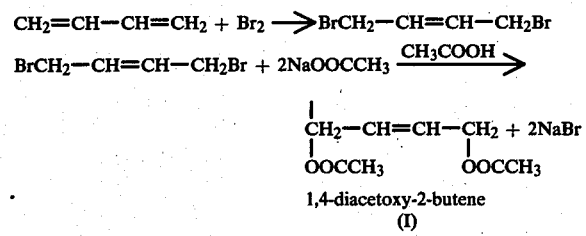

1,4-diacetoxy-2-butene
(I)

Step 2.

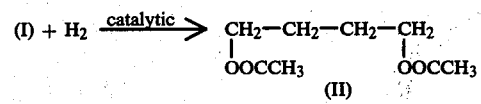

(II)

Step 3.

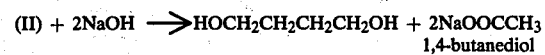

1,4-butanediol

Step 4.

The above steps have been conducted up to and including obtaining 1,4-butanediol as evidenced in the example. The conversion of the alkali metal bromide to produce alkali metal hydroxide and bromine or halogen, as the case may be, is conducted according to known methods for producing halogens. As evident from the examples the separation of 1,4-butanediol was accomplished employing gas-liquid chromatography, please see example III. The separation or recovery of 1,4-butanediol can be accomplished by any means desired, e.g., distillation.

The steps, manner of performing them, and conditions are now generally described. The description of the steps are to be read in conjunction with the remainder of this disclosure including the examples.

Step 1

A halogen is added to a conjugated diene either in a liquid or vapor phase and the formed product immediately allowed to make contact with an alkali metal acetate dissolved or dispersed in an acid, e.g., glacial acetic acid. The diacetate formed from the conjugated diene is dissolved in the acid and the alkali metal halide by-product removed for a latter conversion step to the starting materials, alkali metal acetate and halogen.

The conjugated diene preferably employed in this invention is 1,3-butadiene although the process is applicable to other similar type conjugated dienes, e.g., isoprene, 1,3-pentadiene, 2,3-dimethyl-1,3-butadiene, 2-ethyl-1,3-pentadiene, 1,3-hexadiene, 2-methyl-1,3-hexadiene, 1,3-octadiene, 2-methyl-1,3-undecadiene, 2-methyl-3-isopropyl-1,3-butadiene; and the like.

The halogen preferred in this invention is bromine although chlorine and iodine can also be used. The addition of bromine to butadiene can be conducted in the liquid or vapor phase under atmospheric conditions or under pressure at temperatures broadly ranging from −30° C. to 350° C., the preferred operating temperatures being 100° C. to 250° C. The amount of butadiene employed should be in excess of bromine to prevent the formation of tetrabromoderivatives. The minimum amount is thought to be 1.2 moles of butadiene to 1.0 moles of bromine. It may also be convenient to add a diluent such as nitrogen to the bromine to increase flow rates. The amount of diluent can be, although not limited to, about 2 moles per 1 mole of bromine employed.

Immediately after formation and without separation, the reaction product of butadiene and the halogen is contacted with an alkali metal salt dispersed or dissolved in an organic acid solvent. This is known as the acetolysis step. The cation of the alkali or alkaline earth metal salt in the acetolysis step can be lithium, sodium, potassium, rubidium, cesium, magnesium, calcium, strontium, barium, and ammonium. Here and in the claims "alkali metal" and "alkaline earth metal" are to be read for brevity's sake as being equivalent in the process. The anion portion can be formate, acetate, propionate, butyrate, and the like. The solvent can be formic acid, acetic acid, propionic acid, butyric acid, methanol, butyl acetate and the like. The preferred types of materials employed are sodium or potassium acetate dissolved or dispersed in acetic acid. It is also preferred that the anion portion of the alkali metal salt be the same as that of the organic acid solvent, for example, potassium acetate in acetic acid, potassium propionate in propionic acid, etc. The acetolysis portion of the above-mentioned reaction is a slower reaction than halogenation of a conjugated diene and requires a longer reaction time. Reaction times of 0.5 hrs. to 3.0 hrs. should be sufficient to complete the acetolysis reaction. Pressure could increase the rate of reaction and thus reduce the reaction time. Temperatures ranging from 20° C. to 150° C. should be sufficient for the acetolysis portion of this step but will depend on the boiling point of the organic acid solvent used. Generally, the acetolysis should occur at or near the boiling point of the organic acid solvent being employed.

Step 2

The diacetoxylated alkene formed in the first step is hydrogenated to the corresponding diacetoxylated alkane. The hydrogenation can be conducted batchwise or in a continuous manner, with or without a solvent, at temperatures ranging from 25° C. to 200° C. using various types of hydrogenation catalysts. Hydrogenation catalysts that can be employed are those commonly used in hydrogenation reactions. It is preferred, but not essential, that when palladium on charcoal is used the solvents be limited to methanol, ethanol, or tetrahydrofuran to suppress hydrogenolysis. Examples of suitable solvents are methanol, ethanol, isopropanol, acetic acid, cyclohexane and the like. Butyl acetate enhances hydrogenolysis and is not preferred. Hydrogenation pressures can vary from low, 0.0689 MPa (10 psi) to high 6.89 MPa (1000 psi), but will generally be satisfactory in the 0.172 MPa (25 psi) to 1.034 MPa (150 psi) range. The preferred method utilizes 0.5% palladium on alumina ($Al_2O_3$) at 30° C. under 0.345 MPa (50 psig) hydrogen pressure in a tetrahydrofuran solvent. When the hydrogenation is conducted batchwise, the proportions of materials used can be 5–50 weight percent, preferably 12–25 weight percent diacetoxyalkene dissolved in a suitable solvent using about 0.1–10 weight percent, preferably 0.2–5.0 weight percent catalyst. When the hydrogenation is conducted in a continuous manner, the proportions of materials used can be 5–50 weight percent, preferably 12–25 weight percent diacetoxyalkene dissolved in a suitable solvent and passed over a catalyst bed in a manner consistent with the usual continuous hydrogenation processes. Modifiers such as amines and alkali metal acetates may be employed as required. The hydrogenation step may be conducted before or after the hydrolysis step hereafter described.

Step 3

The diacetoxyalkane (or diacetoxyalkene, depending on whether this step precedes the hydrogenation step) is hydrolyzed to the desired product, dihydroxy alkane (e.g., 1,4-butanediol). This hydrolysis can be conducted under either acid or basic conditions or by transesterification with a lower molecular weight alcohol. In the current invention the hydrolysis is conducted under basic conditions, the preferred reagent being an alkali metal hydroxide (MOH) where M is the same cation as used in the acetolysis step (first step or embodiment) herein described. As in the acetolysis step, M can be lithium, sodium, potassium, cesium, magnesium, calcium, strontium, barium, and ammonium. The hydrolysis is generally conducted by rapidly stirring a heated (50°–100° C., preferably 90°–100° C.) aqueous solution (0.5 to 2.0 molar, preferably 0.8 to 1.5 molar) of an alkali metal hyroxide which contains the diacetoxyalkane (or diacetoxyalkene) in amounts of 5 to 50 weight percent, preferably 7 to 15 weight percent until hydrolysis is complete usually 10 to 60 minutes, depending on concentration and temperatures employed. The amount of alkali metal hydroxide used should be at least 2 moles of hydroxide to 1 mole of diacetoxyalkane. The alkanediol can be separated from the hydrolysis mixture in any suitable manner. For example: the alkanediol can be distilled directly from the mixture, extracted with a solvent and subsequently separated by distillation, or salted out for direct phase separation or easier solvent extraction. The excess water and sodium acetate is recycled back into the appropriate place within the process cycle to be re-used directly or converted into reusable products.

Step 4

A by-product from the total process is collected for conversion to a material that can be re-used. For example, the alkali metal halide obtained in Step 1, wherein the alkali metal acetate and a dihaloalkene are reacted, is dissolved in a solvent (e.g., water) and subjected to an electric current whereupon free halogen (e.g., bromine) is separated for subsequent use in the first step, that is, the reaction of a halogen with a conjugated diene. Hydrogen is also liberated for use in Step 2. In addition to free halogen and hydrogen, the electrolytic process also reforms an alkali metal hydroxide for subsequent use in the hydrolysis step of this invention. Electrolytic cell(s) used in this invention are essentially the same as the diaphragm cells of commerce such as those used in the manufacture of chlorine. This step is shown as 4 in the total process but can be in any convenient position.

EXAMPLE I

The preparation of the diacetoxyalkene (1,4-diacetoxy-2-butene) was effected as follows:

A 5-liter round-bottom flask was fitted with a heating mantle, stirrer, reflux condenser, thermowell, gas inputs and a burette for bromine addition via an electrically heated vaporizer. To the flask was charged 416.8 grams of glacial acetic acid and 98.2 grams potassium acetate. Nitrogen diluent was passed through the vaporizer and above the surface of the liquid at about 1.5 liters per hr. while the contents of the flask were heated to about 123° C. Butadiene was added at a rate of about 4 liters/hr in the vapor phase above the liquid level of the flask. Bromine was slowly added at a rate of about 3 milliliters per hour into the stream of nitrogen diluent, vaporized in the vaporizer and contacted with butadiene in the vapor phase above the liquid level of the flask. The reaction product of bromine and butadiene liquified in the condenser and dropped back into the rapidly stirred liquid phase of potassium acetate and acetic acid whereupon the dibromobutene-2 reacted with potassium acetate to form diacetoxy-2-butene. A total of 63.7 grams of bromine was added in the above-described manner over a five hour period. The temperature of the liquid layer within the flask was maintained about 122° to 126° C. during the reaction. After the addition of bromine was complete, the liquid layer was stirred for about one hour and cooled to ambient room temperature. At this point the products can be separated by distillation. A more rapid means of product analysis is by gas-liquid chromatography (GLC) using a 3.048 m (10 ft) chromatographic column filled with CS-10 packing (Cyanosilicon, Analabs, Inc.) and programed between 150° C. to 220° C. at a rate of 20° C./minute. Approximately 508 grams of effluent was mixed with 35 grams of an internal standard, hexyl acetate, and the stirring stopped to allow all undissolved salts (mainly potassium bromide) to settle. An aliquot sample of the liquid phase was analyzed by GLC as shown:

| Component | Percent of Total Area | Percent Product Distribution |
|---|---|---|
| Hexyl acetate (internal standard) | 7.388 | — |
| trans-1,4-Diacetoxy-2-butene | 9.297 | 79.5 |
| cis-1,4-Diacetoxy-2-butene | 1.771 | 15.2 |
| 3,4-Diacetoxy-1-butene | 0.073 | 0.6 |
| 1,2,3,4-tetraacetoxybutane | 0.550 | 4.7 |
| | | 100.0 |

The amount of product obtained was based on GLC analysis and was calculated according to the following formula:

$$\frac{[(A) + (B) + (C) + (D)]}{\% \text{ Area of internal standard}} \times \text{Relative Weight response of internal standard} \times \text{Weight of Internal Standard} = \text{Total grams of Product}$$

where $A$ = % Area of trans-1,4-Diacetoxy-2-butene
$B$ = % Area of cis-1,4-Diacetoxy-2-butene
$C$ = % Area of 3,4-Diacetoxy-1-butene
$D$ = % Area of 1,2,3,4-tetraacetoxybutane
therefore:
$$\frac{[(9.297) + (1.771) + (0.073) + (2 \times 0.55)]}{7.388} \times 0.89 \times 35 \text{ grams} = 51.6 \text{ grams of products}$$

The amount and mole % yield of products obtained are shown as follows:

| Component | | Product Weight, grams | Mole % Yield* |
|---|---|---|---|
| 1. trans-1,4-Diacetoxy-2-butene | 51.6×0.795= | 41.02 | 59.72 |
| 2. cis-1,4-Diacetoxy-2-butene | 51.6×0.152= | 7.84 | 11.41 |
| 3. 3,4-Diacetoxy-1-butene | 51.6×0.006= | 0.31 | 0.45 |
| 4. 1,2,3,4-Tetraacetoxybutane | 51.6×0.047= | 2.43 | 1.05 |
| | Total | 51.6 | 72.63 |

*Based on amount of bromine charged, 63.7 grams (0.398 moles).

EXAMPLE II

The following is a typical example of batch hydrogenation. A 400 ml Parr pressure bottle was charged with 1,4-diacetoxy-2-butene (30.0 grams, 0.174 moles), 200 ml (177.6 grams) of tetrahydrofuran (THF), 0.2 grams of triethylamine and 0.5 grams of 0.5% palladium on alumina catalyst. The bottle was placed in the shaker, evacuated, flushed three times with hydrogen and pressured to 45 psig. Shaking was started and the pressure drop recorded as a function of time. Hydrogen uptake ceased after 57 minutes. The mixture was removed, filtered, and analyzed by GLC on a 15% tris(2-cyanoethoxy) propane column 0.476 cm (0.187 in)×91.44 cm (3 ft) programed from 100° C. to 170° C. at 10° C./min. The product was found to consist of 97.7% 1,4-diacetoxybutane (1,4-DABA) and 2.3% butyl acetate.

The product was placed in a 300 ml flask and the THF solvent distilled carefully through a 15.24 cm (6 inch) vacuum jacketed column. Solvent free product was transferred to a 100 ml flask fitted with a 15.24 cm (6 inch) column and vacuum distillation apparatus. Only one fraction was taken, b.p. 83°–85° C./1mm.

|  | Net Weight, grams |  |
|---|---|---|
| Fraction 1 | 28.50 | 1,4-DABA (99%) |
| Kettle Residue | 0.50 | 1,4-DABA (66%) |
| Remaining in distillation apparatus | 0.35 |  |
| Total Recovered Material | 29.35 | 96.6 mole % yield |
| Percent of initial charge | 97.81 |  |
| Fraction #1 as percent of charge | 95.0 |  |

EXAMPLE III

The following is a typical example of batch hydrolysis of 1,4-diacetoxybutane to 1,4-butanediol. Sodium hydroxide solution (50 ml, 1.2 molar) was charged to a 150 ml resin flask fitted with a high sheer reciprocating stirrer, heating mantle, reflux condenser and a septum adaptor. The solution was heated to reflux, 1,4-diacetoxybutane (4.3 g, 0.025 moles) and an internal standard, 1,2-propanediol (2.5 g), were added through the septum adaptor. After stirring for the indicated period of time shown below samples were withdrawn and analyzed by GLC using a 274.3 cm (9 ft)×0.476 cm (0.187 in.) OV 225 column (silicon compound containing 25% cyanopropyl and 25% phenyl groups from Ohio Valley, Inc.) programed from 70° C. to 160° C. at a rate of 20° C./min using a FID detector.

| Time Minutes | GLC Area, % | | Mole % Yield of 1,4-Butanediol |
|---|---|---|---|
|  | Propanediol | 1,4-Diol |  |
| 15 | 53 | 47 | 98.8 |
| 30 | 53 | 47 | 98.8 |
| 60 | 52 | 48 | 100.0 |

1,4-Butanediol can also be separated by distillation, b.p. 127° C./20 mm corrected to 230° C./760 mm.

EXAMPLE IV

To typical electrochemical reaction cells (40), generally similar to the chlorine/caustic diaphragm cell of commerce, there is charged an aqueous solution of sodium bromide (or potassium bromide, depending on the alkali metal acetate used in the first step) having an acidity of less than 6.5 pH. The cells are each equipped to collect gaseous hydrogen and bromine and solid sodium hydroxide (preferably as an aqueous solution). The temperature of the cells is maintained between 90°–100° C.

The cathodes are steel and the anodes are dimensionally stable or fabricated from non-graphitic carbon. Approximately 100,000 amperes is passed through each cell that operates at 2.9 volts per cell. The 40 cells would produce the following products that are distributed to the various steps requiring each material:

| Materials Produced | Regenerated Amount | Process Step Utilizing Regenerated Products |
|---|---|---|
| Bromine | $6.94 \times 10^4$ moles/hr | Step 1 |
| Hydrogen | $6.94 \times 10^4$ moles/hr | Step 2 |
| Sodium Hydroxide (in solution) | $13,888 \times 10^4$ moles/hr | Step 3 |

As noted earlier, this example is given, calculated on known electrochemistry.

The bromination (i.e., the addition of bromine to a conjugated diene) advantageously can be conducted in a separate operation and the dibromo-alkene recovered. Conducting the bromination (i.e., according to the first equation shown for step 1) in the absence of an alkali metal salt (shown in the second equation of step 1) substantially improved ultimate yields.

Reasonable variation and modification are possible in the scope of the foregoing disclosure and the appended claims to the invention, the essence of which is that there have been conceived a series of steps in combinations as described for the production of an alkanediol, generally using only a conjugated diene, together with a halogen, an alkali metal acetate, an acid as reactants, with conversion of alkali metal halide, formed in the process with water electrochemically producing alkali metal hydroxide and halogen for use in other steps of said process.

I claim:
1. The production of an alkanediol which comprises bringing together in a reaction zone in vapor phase a conjugated diene and a halogen selected from chlorine and bromine, then immediately reacting in said reaction zone the reaction product thus obtained with a liquid mixture of an alkali metal acetate and an organic acid solvent under conditions to form a 1,4-diacetoxyalkene, hydrogenating said 1,4-diacetoxyalkene to the corresponding alkane and hydrolyzing said alkane to the corresponding 1,4-alkanediol; the vapor phase reaction being effected above the liquid level of said mixture of said acetate and said acid in said reaction zone.

2. A process according to claim 1 wherein the conjugated diene is at least one selected from 1,3-butadiene, isoprene, 1,3-pentadiene, 2,3-dimethyl-1,3-butadiene, 2-ethyl-1,3-pentadiene, 1,3-hexadiene, 2-methyl-1,3-hexadiene, 1,3-octadiene, 2-methyl-1,3-undecadiene, 2-methyl-3-isopropyl-1,3-butadiene.

3. A process according to claim 1 wherein the conjugated diene is 1,3-butadiene.

4. A process according to claim 1 wherein the reactants are 1,3-butadiene, sodium acetate, acetic acid and a halogen selected from chlorine and bromine, the process is effected in a manner and under conditions to produce 1,4-diacetoxy-2-butene which is hydrogenated to form the alkane which then is hydrolyzed to form 1,4-butanediol.

5. A process according to claim 1 wherein the reactants are 1,3-butadiene, sodium acetate, acetic acid and a halogen selected from chlorine and bromine, the process is effected in a manner and under conditions to produce 1,4-diacetoxy-2-butene which is hydrolyzed to form the 1,4-butenediol which is and then hydrogenated to form 1,4-butanediol.

* * * * *